United States Patent
Kang et al.

(10) Patent No.: US 12,163,114 B2
(45) Date of Patent: Dec. 10, 2024

(54) CELL CULTURE RECEPTACLE

(71) Applicant: KOREA RESEARCH INSTITUTE OF CHEMICAL TECHNOLOGY, Daejeon (KR)

(72) Inventors: Sun Woong Kang, Daejeon (KR); Sang Soo Han, Daejeon (KR); Cho Rok Jung, Daejeon (KR); Kyung Sook Chung, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 1075 days.

(21) Appl. No.: 16/330,608

(22) PCT Filed: Sep. 6, 2017

(86) PCT No.: PCT/KR2017/009734
§ 371 (c)(1),
(2) Date: Oct. 2, 2020

(87) PCT Pub. No.: WO2018/048181
PCT Pub. Date: Mar. 15, 2018

(65) Prior Publication Data
US 2021/0017483 A1  Jan. 21, 2021

(30) Foreign Application Priority Data
Sep. 6, 2016 (KR) .......................... 10-2016-0114379

(51) Int. Cl.
*C12M 1/06* (2006.01)
*C12M 1/32* (2006.01)

(52) U.S. Cl.
CPC ............ *C12M 27/02* (2013.01); *C12M 23/12* (2013.01)

(58) Field of Classification Search
CPC ....... C12M 23/12; C12M 25/04; C12M 27/02
See application file for complete search history.

(56) References Cited

U.S. PATENT DOCUMENTS 2,958,517 A * 11/1960 De Long ............. B01F 33/4533
422/566
4,888,294 A * 12/1989 Van Wezel ............. C12M 33/10
435/295.3

(Continued)

FOREIGN PATENT DOCUMENTS

CN  102108333 A  6/2011
CN  105820952 A  8/2016

(Continued)

OTHER PUBLICATIONS

Mitsuo, O., et al., JP-2003135056-A, published May 13, 2003, original and machine translation (Year: 2003).*

(Continued)

*Primary Examiner* — Elizabeth A Robinson
*Assistant Examiner* — Jonathan E Lepage
(74) *Attorney, Agent, or Firm* — RAPHAEL BELLUM PLLC

(57) ABSTRACT

A cell culture vessel according to the present invention is characterized by comprising a first vessel having a stirring member disposed therein, and a second vessel configured to be inserted in the interior of the first vessel and having a hole for allowing a solvent accommodated in the first vessel to pass through the interior thereof, wherein the stirring member is arranged in a recess portion formed in the first vessel.

7 Claims, 16 Drawing Sheets

(56) References Cited

U.S. PATENT DOCUMENTS

| | | | |
|---|---|---|---|
| 5,019,512 A * | 5/1991 | Varecka | C12M 29/04 |
| | | | 435/813 |
| 2009/0137026 A1 * | 5/2009 | Kobayashi | C12M 41/00 |
| | | | 435/286.4 |
| 2009/0202589 A1 | 8/2009 | Muller et al. | |

FOREIGN PATENT DOCUMENTS

| | | | | |
|---|---|---|---|---|
| JP | 05252933 A | 10/1993 | | |
| KR | 1020080020622 A | 3/2008 | | |
| WO | 9011345 A1 | 10/1990 | | |
| WO | WO-2005118141 A2 * | 12/2005 | | B01D 65/08 |

OTHER PUBLICATIONS

International Search Report in International Application No. PCT/KR2017/009734, dated Mar. 19, 2018.

\* cited by examiner

CELL CULTURE RECEPTACLE

TECHNICAL FIELD

The present invention relates to a cell culture vessel which can carry out an adhesion and suspension culture.

BACKGROUND ART

Nowadays, with the expansion of cell therapy techniques using cultured cells for treating diseases, interest in a cell culture is increasing. Such in vitro culture requires various culture devices and conditions to provide a similar culture environment to the body.

One important factor in this regard is a cell culture vessel. Such cells which are artificially cultured grow in an adhesion or suspension state. In the case of animal cells, most of the cells except for the blood-based cells grow in the adhesion state. These adherent culture cells require a surface coated with extracellular matrix components, for example, a tissue culture dish so as to increase an adherent property.

A conventional cell culture vessel is equipped with a stirring member to continuously stir a cell liquid when performing the suspension culture. However, this stirring member is disposed to protrude on the bottom surface of the cell culture vessel, which results in the reduction of the space in which the cells float during the suspension culture. In addition, the cell adhesion does not occur on the bottom surface of the cell culture vessel, thereby decreasing the efficiency of the adhesion culture.

DETAILED DESCRIPTION OF THE INVENTION

Technical Problem

One exemplary object according to embodiments of the present invention is to provide a cell culture vessel that increases the efficiency of an adhesion and suspension culture.

Means for Solving the Problem

A cell culture vessel according to an embodiment of the present invention is characterized by comprising a first vessel having a stirring member disposed therein, and a second vessel configured to be inserted in the interior of the first vessel and having a hole for allowing a solvent accommodated in the first vessel to pass through the interior thereof, wherein the stirring member is arranged in a recess portion formed in the first vessel.

In an embodiment, the area of the recess portion may be set to sufficiently accommodate the stirring member in the recess portion and to cause a cell adhesion to occur on the bottom portion of the first vessel.

In an embodiment, the area of the recess portion may be 70% or less of the area of one surface of the first vessel.

In an embodiment, a third vessel may be arranged in the interior of the second vessel, and the third vessel may include a hole for allowing a solvent accommodated in the second vessel to pass through the interior thereof.

In an embodiment, the stirring member may be a magnetic stirrer.

In an embodiment, a plurality of the first vessels may be provided and integrally formed on a plate.

In an embodiment, an upper end of the second vessel may be provided with a latching portion configured to be caught to the first vessel.

Effects of the Invention

According to the embodiment of the present invention, since the stirring member is disposed in the recess portion formed in the inner wall of the cell culture vessel, the inner wall can be utilized as a space for performing the adhesion culture. Accordingly, it is possible to increase the number of cells capable of performing the adhesion culture.

Further, according to the embodiment of the present invention, since the stirring member is disposed in the recess portion, the space in which the cells are floated can be increased. In addition, it is possible to minimize the number of cells adhered to the stirring member. Accordingly, the efficiency of the suspension culture can be increased.

Furthermore, the cell culture vessel according to the embodiment of the present invention can be applied to 6-well, 12-well and 24-well plates which are mainly used in a laboratory, and can also be applied to a small amount of the cell culture.

Still furthermore, the cell culture vessel according to the embodiment of the present invention can be applied to a co-culture, a direct/indirect culture, and 3D culture techniques.

TYPE FOR CARRYING OUT THE INVENTION

Figure 1:
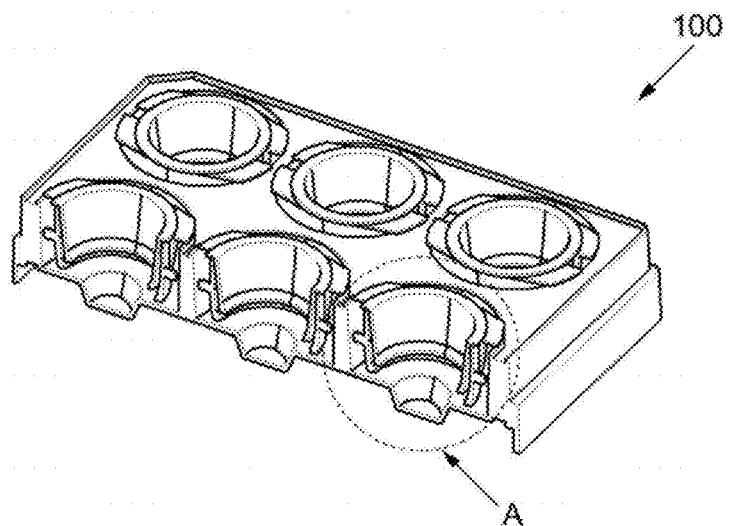
FIG. 1 is a perspective view of a cell culture vessel associated with an embodiment of the present invention.

Hereinafter, the embodiments described in the specification of the subject application will be explained in details with reference to the accompanying drawings, wherein like or similar constitutive elements are denoted by the same reference numerals and duplicate descriptions thereof will be omitted. The suffixes "module" and "part" for the constitutive elements used in the following description are given or mixed only in consideration of ease writing of the specification and do not have their own meanings or roles which are distinguished from each other. Further, in the following description of the embodiments of the present invention, a detailed description for related and known technologies will be omitted if it is determined that the gist of the embodiments disclosed herein may be blurred. Furthermore, it should be understood that the accompanying drawings are merely to aid in the easy understanding of the embodiments disclosed herein without limiting the technical scope of the invention disclosed herein by the accompanying drawings, and cover all of modifications, equivalents and alternatives which come within the spirit and scope of the invention.

The terms containing ordinal numbers such as first, second, etc., may be used to illustrate various constitutive elements, but the constitutive elements are not limited to those terms. The above terms are used only for the purpose of distinguishing one constitutive element from the other one.

It should be understood that when a certain constitutive element is referred to be "connected" or "accessed" to the other one, it may be directly connected or accessed to the other constitutive element but any another element may be interposed between them. On the other hand, it should be understood that when a certain constitutive element is referred to be "directly connected" or "directly accessed" to the other one, there is no another element between them.

The singular expressions may include plural expressions unless the context clearly dictates otherwise.

Further, it will have to be understood that as disclosed in the specification of the subject application, the terms "comprises", "having", and the like are intended to specify that a feature, a number, a step, an operation, a constitutive element, a component or a combination thereof is in existence, but not to exclude the presence or addition of one or more other features, numbers, steps, operations, constitutive elements, components or combinations thereof.

Hereinafter, the cell culture vessel related to the present invention will be described in detail with reference to the drawings.

Figure 2:
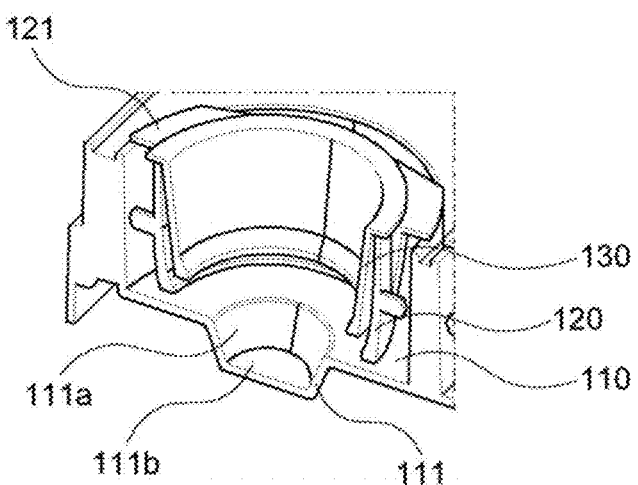
FIG. 2 is an enlarged view of the portion A shown in FIG. 1.
Figure 3:
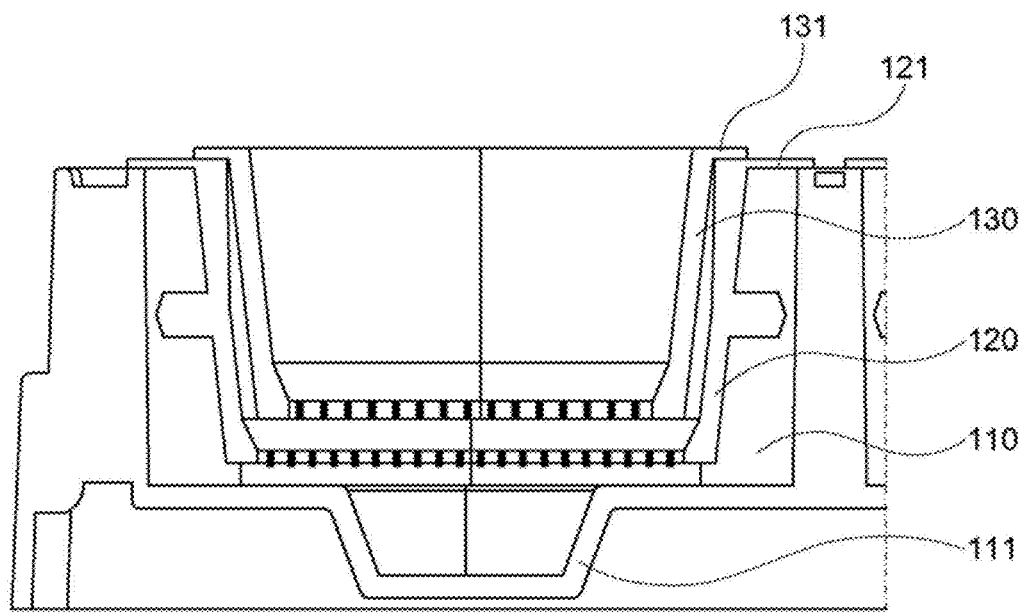
FIG. 3 is a cross-section view of a cell culture vessel.

FIG. 1 is a perspective view of a cell culture vessel according to an embodiment of the present invention, and FIG. 2 is an enlarged view of the portion A shown in FIG. 1. In addition, FIG. 3 is a cross-section view taken along the line B-B shown in FIG. 1.

Referring to FIG. 1, a cell culture vessel 100 may comprise first and second vessels 110 and 120.

The first vessel 110 is the portion forming a plate of the cell culture vessel 100.

More concretely, a plurality of the first vessels 110 may be integrally formed in one plate. In other words, one plate may include 6, 12 and 24 first vessels 110. The drawings illustratively show one plate including 6 first vessels 110, but the present invention is not limited thereto.

In the other embodiment, the first vessel may be a well-typed vessel as well as a dish-typed vessel such as a multi-insert dish. Alternatively, a plurality of the inserts may be inserted into one well (or dish).

Further, the first vessel 110 may be arranged in various forms on the plate. Although the drawings show only the examples arranged in a matrix form, the present invention may comprise the first vessel arranged in various forms such as a concentric circle shape without being limited thereto.

A stirring member 140 is disposed in the first vessel 110.

The stirring member may be provided of a magnetic stirrer. The magnetic stirrer may be made of a magnetic material. This stirring member may be configured to rotate under the influence of the magnetic field applied on the outside of the first vessel 110.

A recess portion 111 may be disposed in the interior of the first vessel 110. The recess portion 111 may be formed in any one of a plurality of the inner walls defining the first vessel 110.

For example, the recess portion 111 may be formed on the bottom surface of the first vessel 110. That is, the recess portion 111 may be formed from the bottom surface of the first vessel 110 toward the outer side of the first vessel 110.

Meanwhile, the recess portion may be referred to as a dent portion.

The area of the recess portion 111 may be 70% or less of the area of one surface (e.g., bottom surface) of the first vessel 110. Such area of the recess portion 111 can sufficiently accommodate the magnetic stirrer in the recess portion 111 and cause cell adhesion to occur on the bottom surface of the first vessel. On the other hand, the diameter of the bottom surface of the first vessel may be as shown in the following table.

TABLE 1

| Article | 6 well | 12 well | 24 well | 35 mm | 60 mm |
|---|---|---|---|---|---|
| Bottom diameter (mm) | 35 | 21.9 | 15.5 | 35 | 52.8 |

On the other hand, the height of the recess portion 111 can be designed in consideration of a manufacturing manner of the cell culture vessel, a clearance space for fastening the inserts and an internal capacity of the well plate. For example, the height of the recess portion may be about 20 to 25 mm on the basis of a 6-well in consideration of length adjustment of the inserts and the like.

More specifically, the recess portion 111 may include first and second surfaces 111a and 111b. The first and second surfaces 111a and 111b are connected to each other. The first surface 111a may be configured to substantially intersect with the bottom surface of the first vessel 110. The second surface 111b may be configured to be substantially parallel to the bottom surface of the first vessel 110.

The above-described stirring member may be disposed on the second surface 111b of the recess portion 111. More specifically, the magnetic stirrer is disposed on the second surface 111b such that the longitudinal direction thereof is parallel to the second surface 111b. The magnetic stirrer may be rotated around the center thereof, and the rotating surface of the magnetic stirrer may be substantially parallel to the second surface 111b.

Referring to FIG. 2, the second vessel 120 may be configured to be inserted in the interior of the first vessel 110. In this case, the height of the second vessel 120 may be formed to be smaller than the height of the first vessel 110 so that the bottom surfaces of the second vessel 120 and the first vessel 110 do not contact each other.

Due to the above configuration, the space formed between the bottom surfaces of the first and second vessels 110 and 120 can be utilized used as a space for performing a suspension culture, as will be described in detail later with reference to FIG. 5.

The second vessel 120 may have a latching portion 121 formed at an upper end thereof so as to be caught to the first vessel 110. The upper ends of the first and second vessels 110 and 120 may be disposed on substantially the same plane as the latching portion 121 is configured to be caught to the first vessel 110.

Figure 4A:
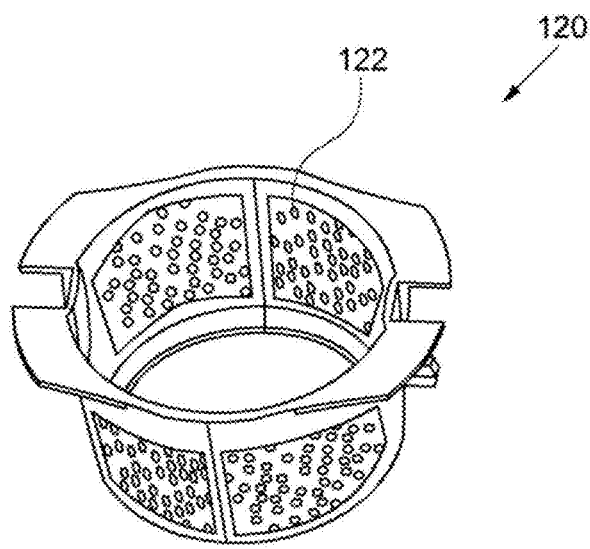
FIGS. 4a and 4b are views showing each of a second and a third vessels related to an embodiment of the present invention.

Referring to FIG. 4a, the second vessel 120 may include a hole 122 to allow a solvent accommodated in the first vessel 110 to pass through the interior thereof. Specifically, a plurality of the holes 122 may be uniformly formed on at least one of the bottom surface and the side surface of the second vessel.

For example, FIG. 3 shows a plurality of the holes distributed on the bottom surface of the second vessel, and FIG. 4a shows that a plurality of the holes is distributed on the side surface of the second vessel.

The diameter of the hole is about 0.4 to 8 μm and the density of the hole is about $10^5$ to $10^8/cm^2$.

In addition, at least a part of the second vessel may be formed of a membrane or a mesh.

Meanwhile, the cell culture vessel may further comprise a third vessel 130. The third vessel 130 is configured to be disposed in the interior of the second vessel 120. In other words, the third vessel 130 may be configured to be smaller than the width and height of the second vessel 120.

Figure 4B:
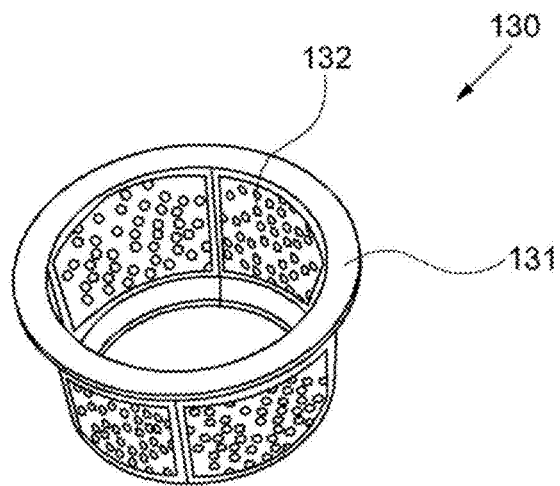

Referring to FIG. 4b, the third vessel 130 may include a hole 132 to allow a solvent accommodated in the second vessel 120 to pass through the interior thereof. Specifically, a plurality of the holes 132 may be uniformly formed on at least one of the bottom surface and the side surface of the third vessel.

In addition, at least a part of the third vessel may be formed of a membrane or a mesh. Meanwhile, the third vessel 130 in FIG. 4b shows the holes formed only on the side surface of the vessel without having any holes on the bottom surface, but the present invention is not limited thereto. That is, the third vessel 130 may have the bottom surface and holes may be formed on the bottom surface (see FIG. 3).

Meanwhile, the size of the hole formed in the second vessel 120 may be different from the size of the hole formed in the third vessel 130. According to such a configuration, any one of the second and third vessels 120 and 130 may have cells not included in the other vessel.

The third vessel 130 may also have a latching portion 131 formed at an upper end thereof so as to be caught to the second vessel 120. The upper ends of the second and third vessels 120 and 130 may be disposed on substantially the same plane as the latching portion 131 is configured to be caught to the second vessel 120.

FIGS. 5a to 5f are views showing the use state of a cell culture vessel according to an embodiment of the present invention.

Hereinafter, the first to fourth cells will be described as an example. At least one of the first to fourth cells may be Hepatocytes growing on Cytodex.

Figure 5A:
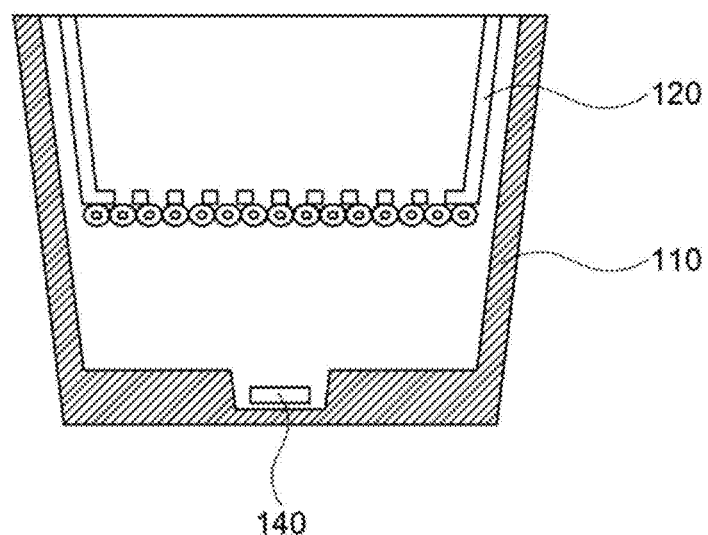
FIGS. 5a to 5f are views showing the use state of a cell culture vessel related to an embodiment of the present invention.

FIG. 5a shows that the cells are adhered and cultured beneath the bottom surface of the second vessel 120 in the cell culture vessel.

Figure 5B:
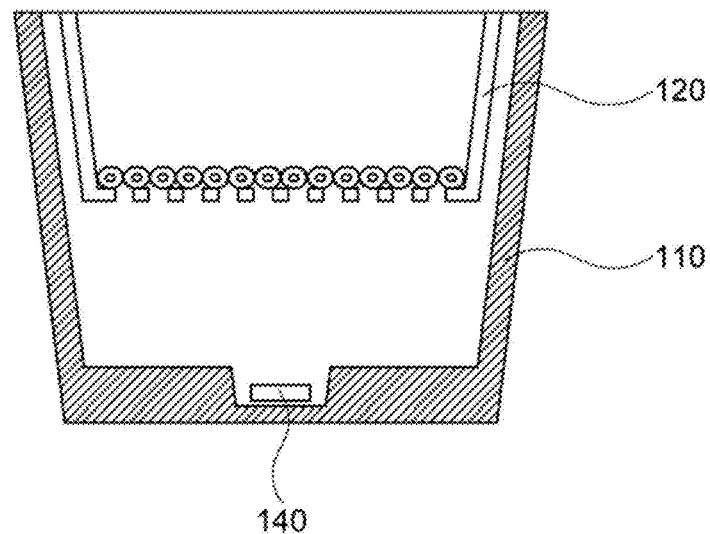

FIG. 5b shows that the cells are adhered and cultured above the bottom surface of the second vessel 120 in the cell culture vessel.

Figure 5C:
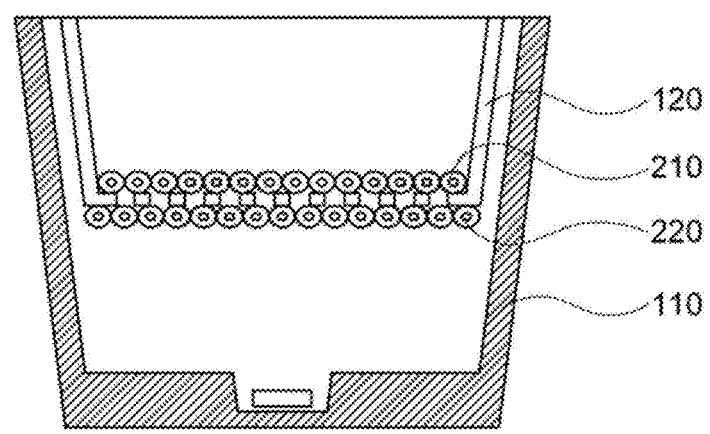

FIG. 5c shows that the cells are adhered and cultured above and beneath the bottom surface of the second vessel 120 in the cell culture vessel.

In FIG. 5c, the cells adhered above the bottom surface of the second vessel 120 may be first cells 210, and the cells adhered beneath the bottom surface may be second cells 220. In this case, the first cells 210 are accommodated to the interior of the second vessel 120, and the second cells 220 are accommodated to the interior of the first vessel 110.

Figure 5D:
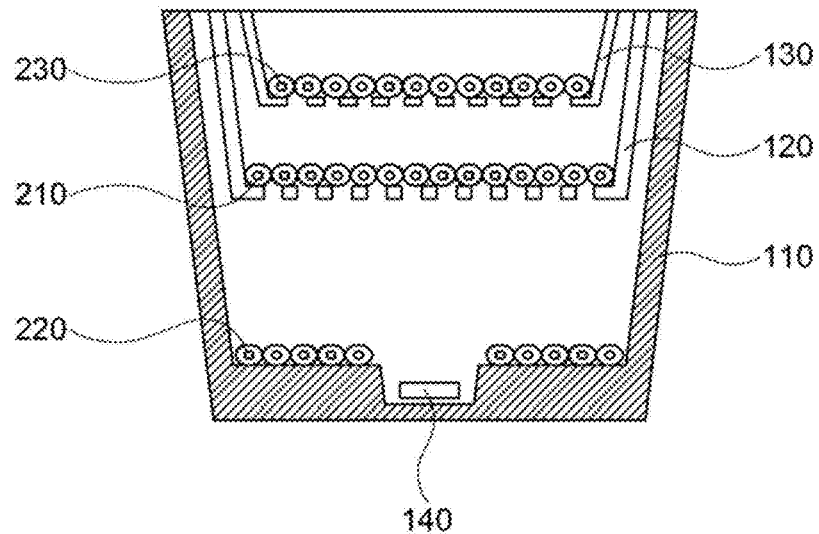

FIG. 5d shows that at least one of the first to third cells 210, 220 and 230 is adhered and cultured on the bottom surface of the first to third vessels 110, 120 and 130 in the cell culture vessel.

The second cells 220 are adhered and cultured on the bottom surface of the first vessel 110, and the first cells 210 are adhered and cultured on the bottom surface of the second vessel 120. The third cells 230 are adhered and cultured on the bottom surface of the third vessel 130.

Figure 5E:
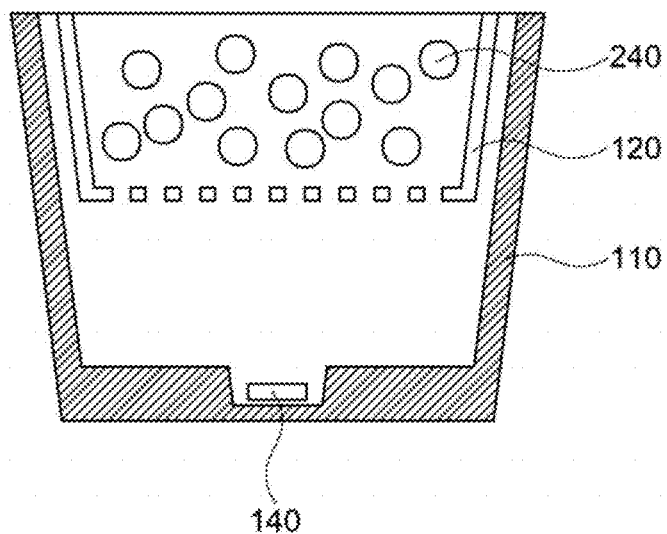

FIG. 5e shows that the fourth cells 240 are suspended and cultured in the interior of the second vessel 120.

Figure 5F:
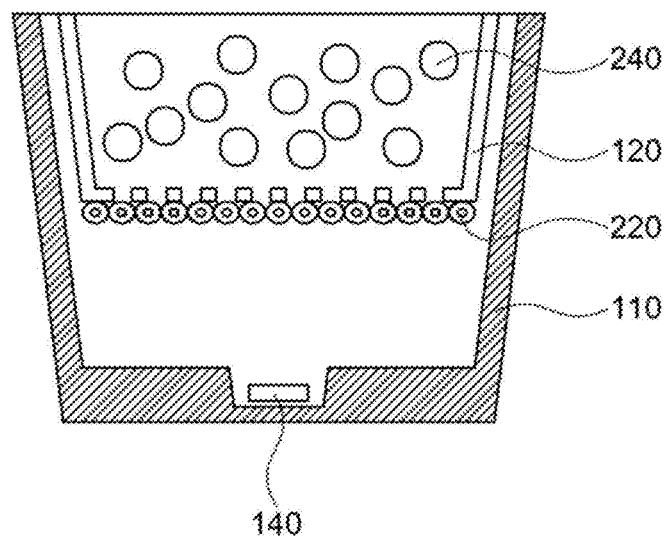

FIG. 5f illustrates that the fourth cells 240 are suspended and cultured in the interior of the second vessel 120 and the second cells 220 are adhered and cultured beneath the bottom surface of the second vessel 120.

According to the embodiment of the present invention, since the stirring member 140 is disposed in the recess portion 111 formed in the inner wall of the cell culture vessel, the inner wall can be utilized as a space for performing the adhesion culture. Accordingly, it is possible to increase the number of the cells capable of performing the adhesion culture.

Further, according to the embodiment of the present invention, since the stirring member 140 is disposed in the recess portion 111, the space in which the cells are suspended can be increased. In addition, it is possible to minimize the number of the cells adhered to the stirring member. Accordingly, the efficiency of the suspension culture can be increased.

The cell culture vessel as described above is not limited to the configurations and the methods of the embodiments described above, but all or a part of the embodiments may be selectively combined so that various modifications may be made by the embodiments.

EXPERIMENTAL EXAMPLE

A cell proliferation was confirmed using the cell culture vessel according to one embodiment of the present invention.

Figure 6A:
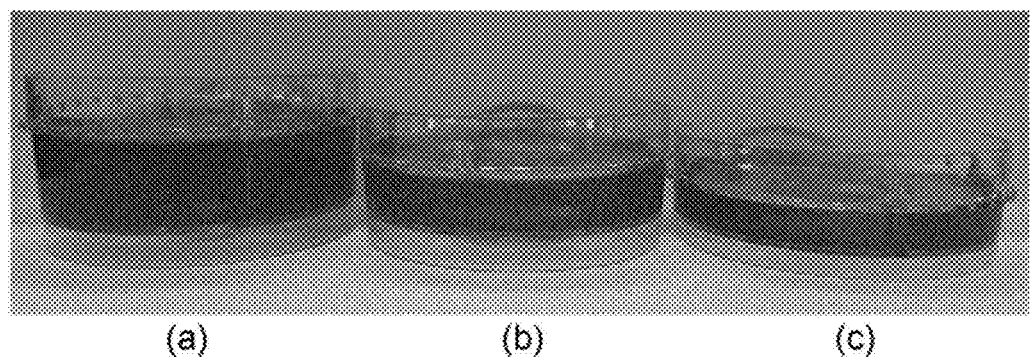
FIGS. 6a and 6b are views and graphs showing the capacity of a cell culture vessel according to the experimental example of the present invention.
Figure 6A:
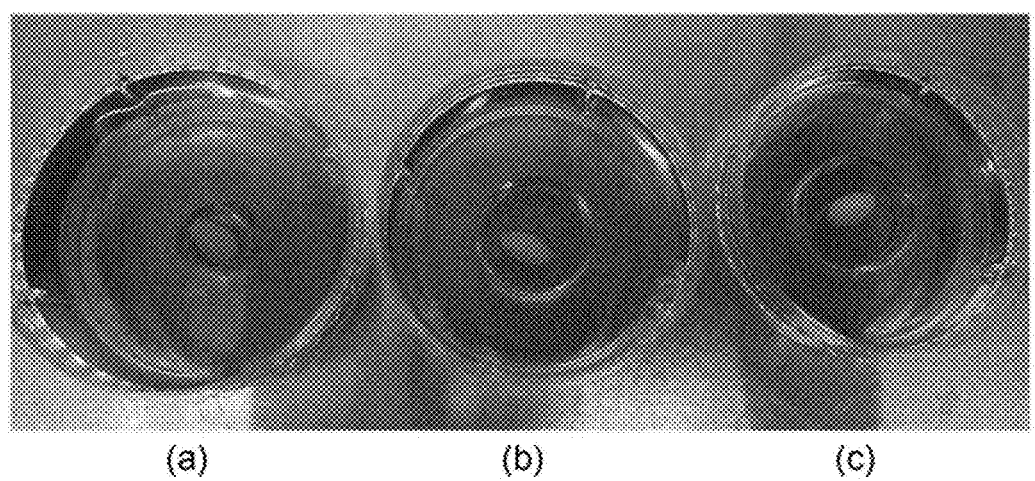
Figure 6B:
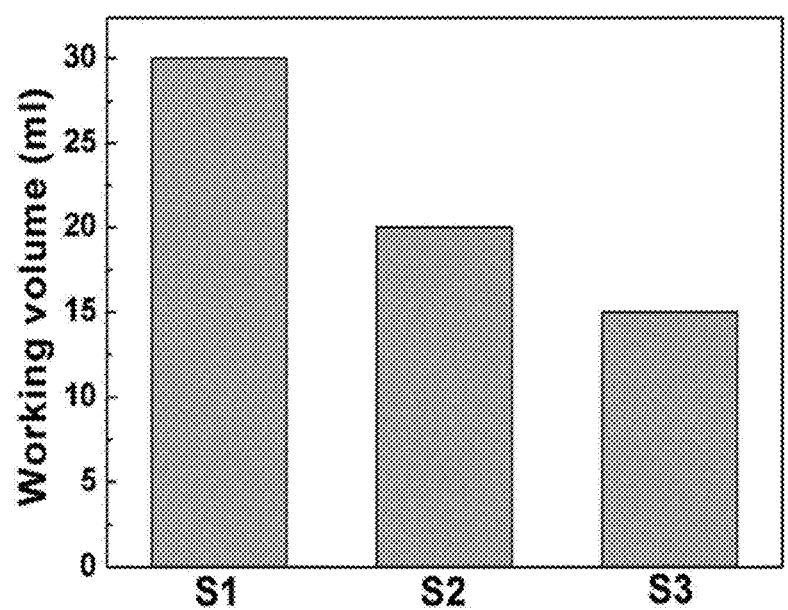

FIGS. 6a and 6b are views and graphs showing the capacity of a cell culture vessel according to the experimental example of the present invention.

FIGS. 6a (a), 6a (b) and 6a (c) show cell culture vessels each having the same diameter of 60 mm. Each of the cell culture vessels shown in FIGS. 6a (a), 6a (b) and 6a (c) has different heights of 25 mm, 20 mm and 15 mm. Further, each of the cell culture vessels shown in FIGS. 6a (a), 6a (b) and 6a (c) is provided with a recess portion having a diameter of 10 mm, 20 mm and 20 mm, and a stirring member is mounted in the recess portion.

Referring to FIG. 6b, there is shown a capacity of the culture media which are run in the cell culture vessels of FIGS. 6a (a), 6a (b) and 6a (c). In the culture vessels of FIGS. 6a (a), a (b) and a (c), the media were run in the capacity of 30 ml, 20 ml and 15 ml.

Hereinafter, the cell culture vessels shown in (a), (b) and (c) of FIG. 6a operated with the above mentioned capacity of the culture media are referred to as sample 1, sample 2 and sample 3 (S1, S2 and S3).

Figure 7A:
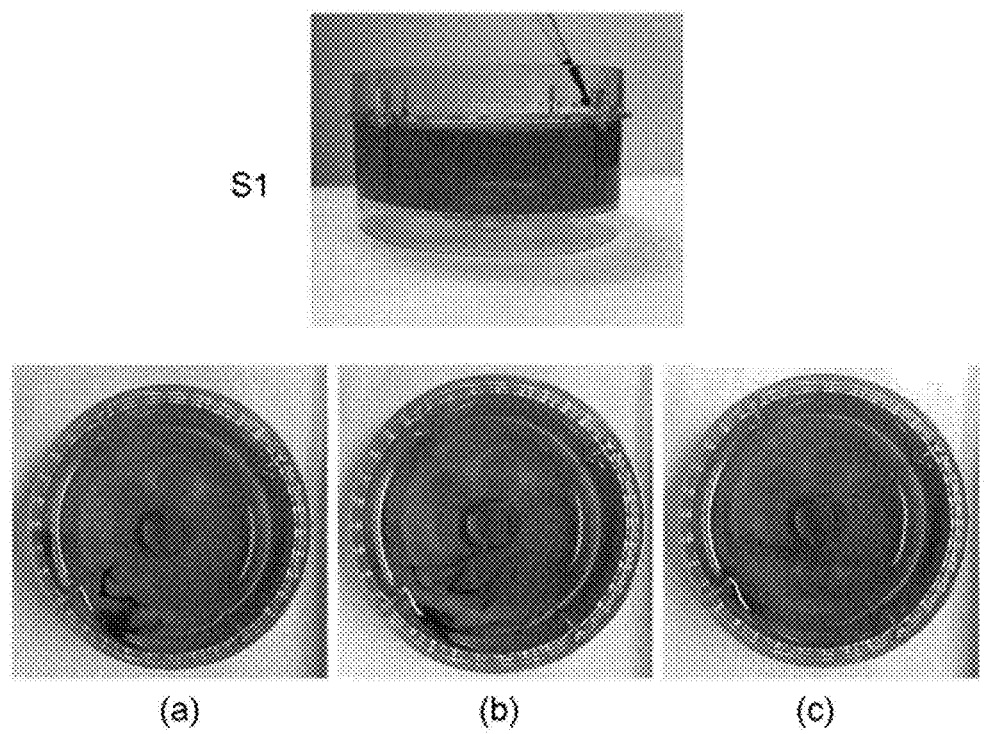
FIGS. 7a, 7b and 7c are views showing the degree of circulation of the media of a sample 1, a sample 2 and a sample 3 using a trepan-blue staining reagent under a static culture condition.
Figure 7B:
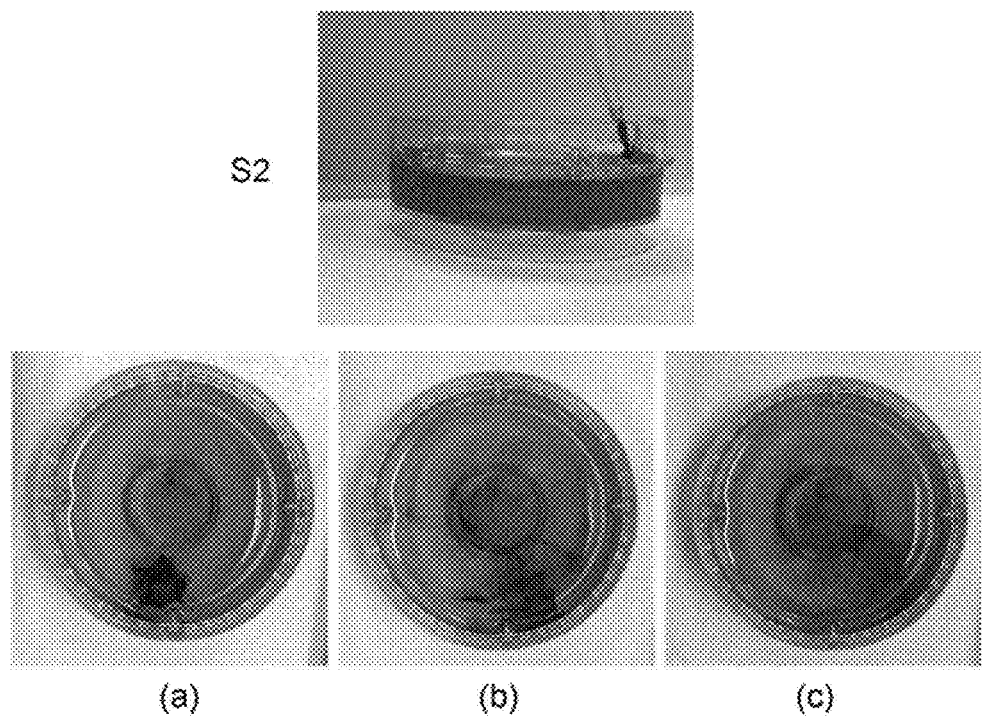
Figure 7C:
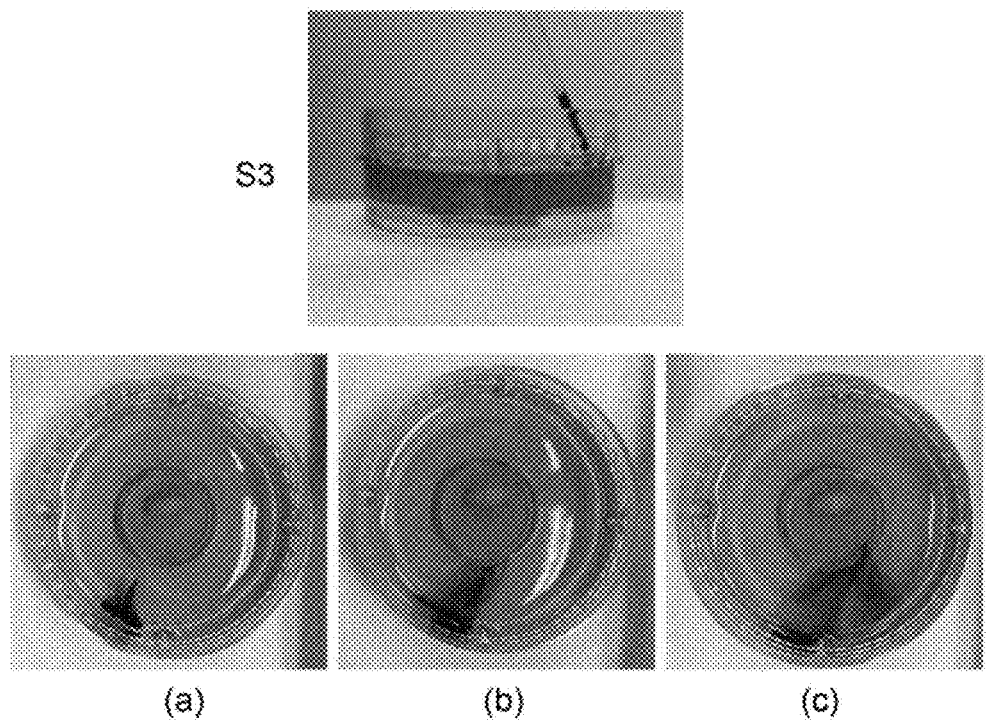

FIGS. 7a, 7b and 7c are views showing the degree of circulation of the media of sample 1, sample 2 and sample 3 using a trepan-blue staining reagent under a static culture condition.

Under the static culture condition, the stirring member is not rotated.

FIGS. 7a (a), a (b) and a (c) are views showing a trepan-blue staining reagent circulated after 1 min, 5 min and 10 min in the static culture condition without stirring, after 10 μl of the trepan-blue staining reagent is injected along the wall surface of the vessel in sample 1.

FIGS. 7b(a), b(b) and b(c) are views showing a trepan-blue staining reagent circulated after 1 min, 5 min and 10 min in the static culture condition without stirring, after 10 μl of the trepan-blue staining reagent is injected along the wall surface of the vessel in sample 2.

FIGS. 7c(a), c(b) and c(c) are views showing a trepan-blue staining reagent circulated after 1 min, 5 min and 10 min in the static culture condition without stirring, after 10 μl of the trepan-blue staining reagent is injected along the wall surface of the vessel in sample 3.

In both of FIGS. 7a, 7b and 7c, it was confirmed that the trepan-blue staining reagents were diffused over a wider area as time elapsed.

FIGS. 8(a), 8(b) and 8(c) are views showing the media circulated after 0 min (immediately after), 1 min and 5 min in a dynamic culture condition, after 10 μl of a trepan-blue staining reagent is injected along the wall surface of the vessel in samples 1 to 3.

Herein, the dynamic culture condition may mean that the stirring member is rotated at 100 rpm. The stirring member may be made of a magnetic stirrer having a diameter of 1 cm.

Figure 8:
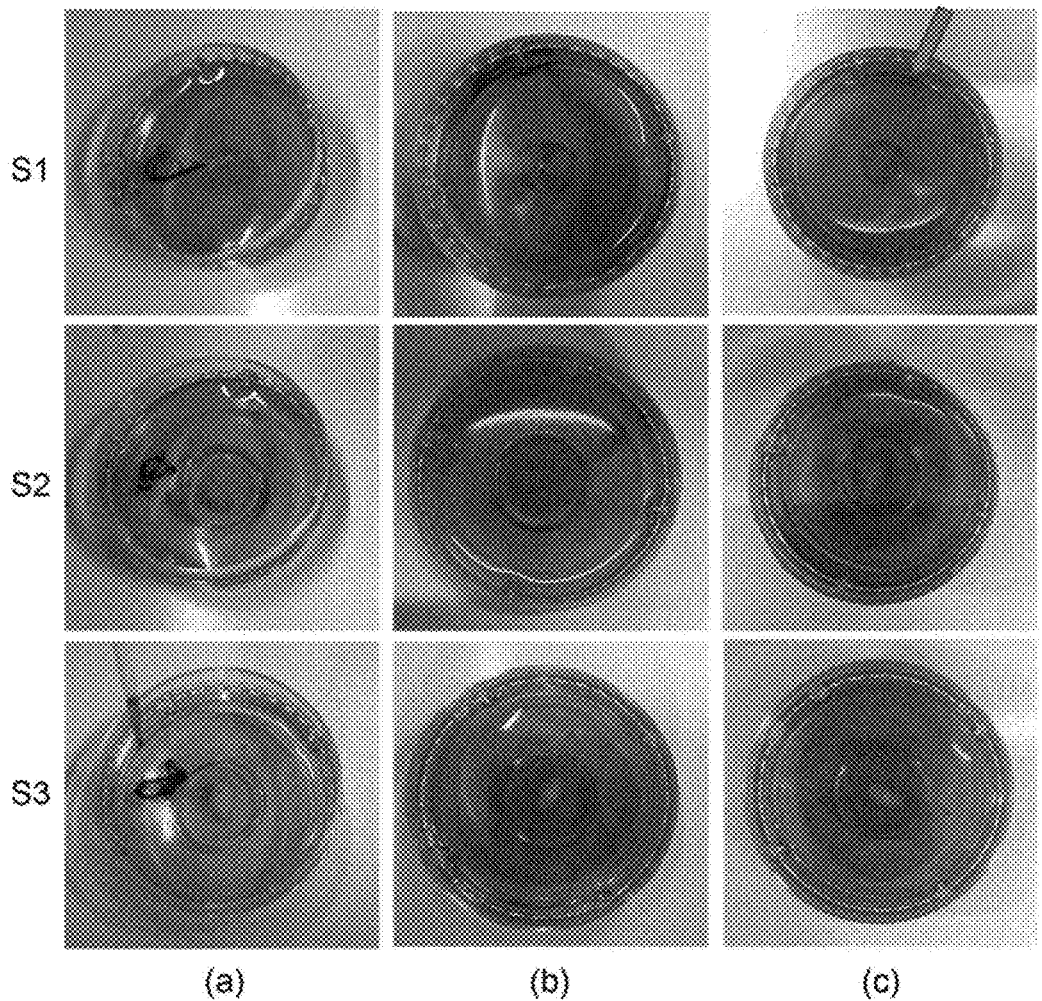
FIG. 8 is views showing the media circulated after 0 min (immediately after), 1 min and 5 min in a dynamic culture condition after 10 µl of a trepan-blue staining reagent is injected along the wall surface of the vessel in samples 1 to 3.

When FIGS. 7a to 7c are compared with FIG. 8, it can be seen that the trepan-blue staining reagent is more rapidly diffused under the dynamic culture condition than under the static culture condition. That is, the circulation of the medium becomes more active in the dynamic culture condition.

Figure 9:
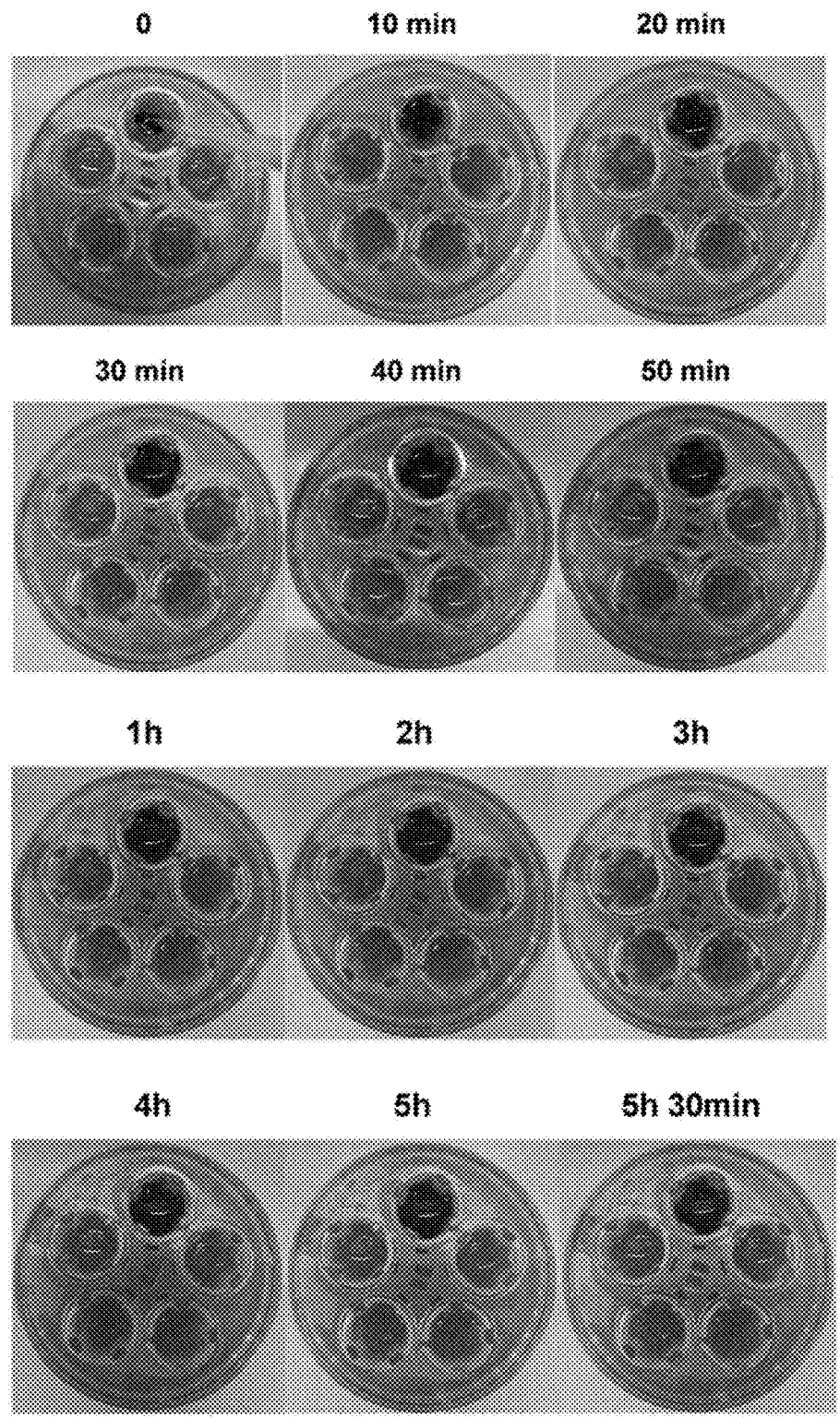
FIGS. 9 to 11 are views illustrating circulation of the media of samples 1 to 3 in which trans-wells are inserted, using a trepan-blue staining reagent under a dynamic culture condition.
Figure 10:
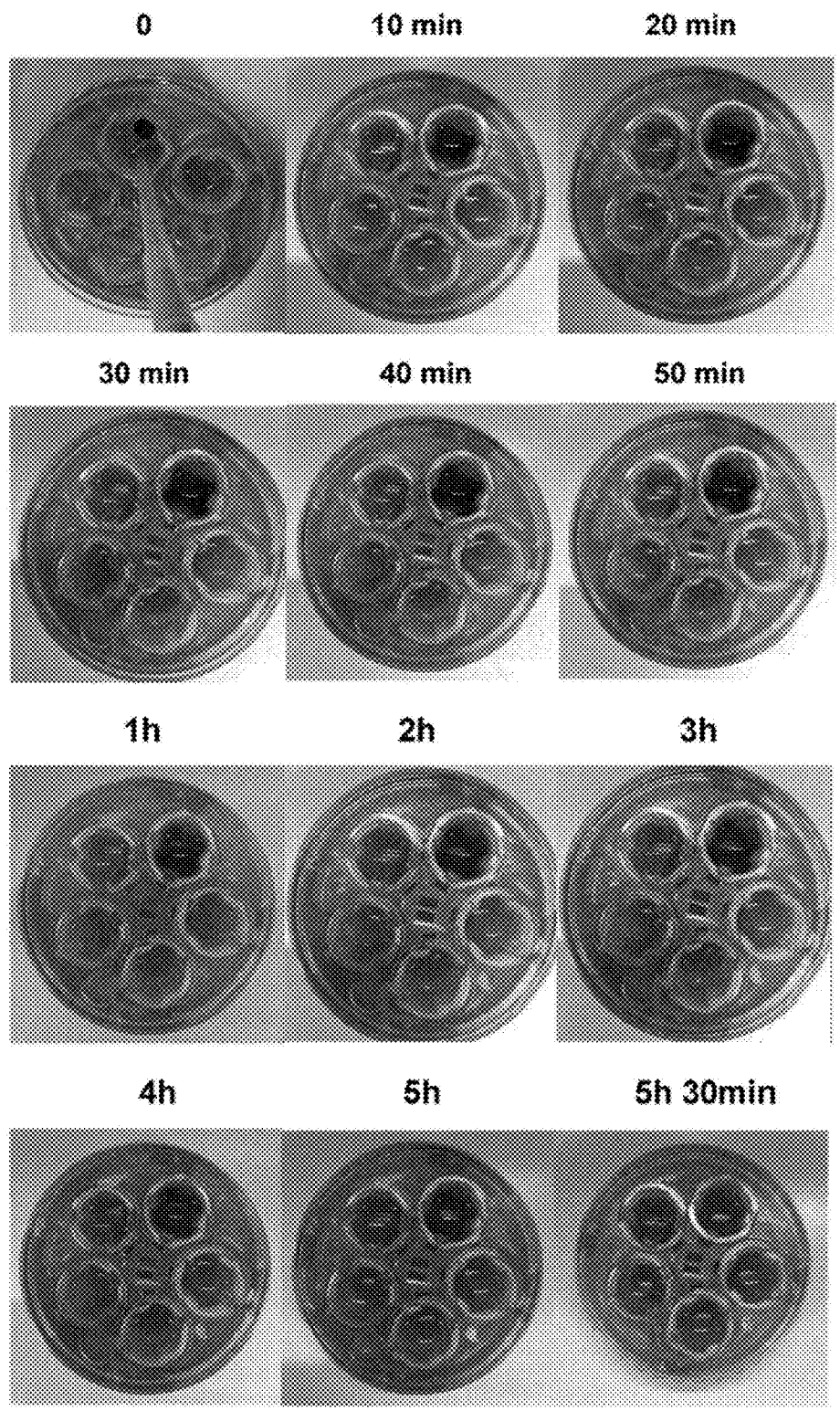
Figure 11:
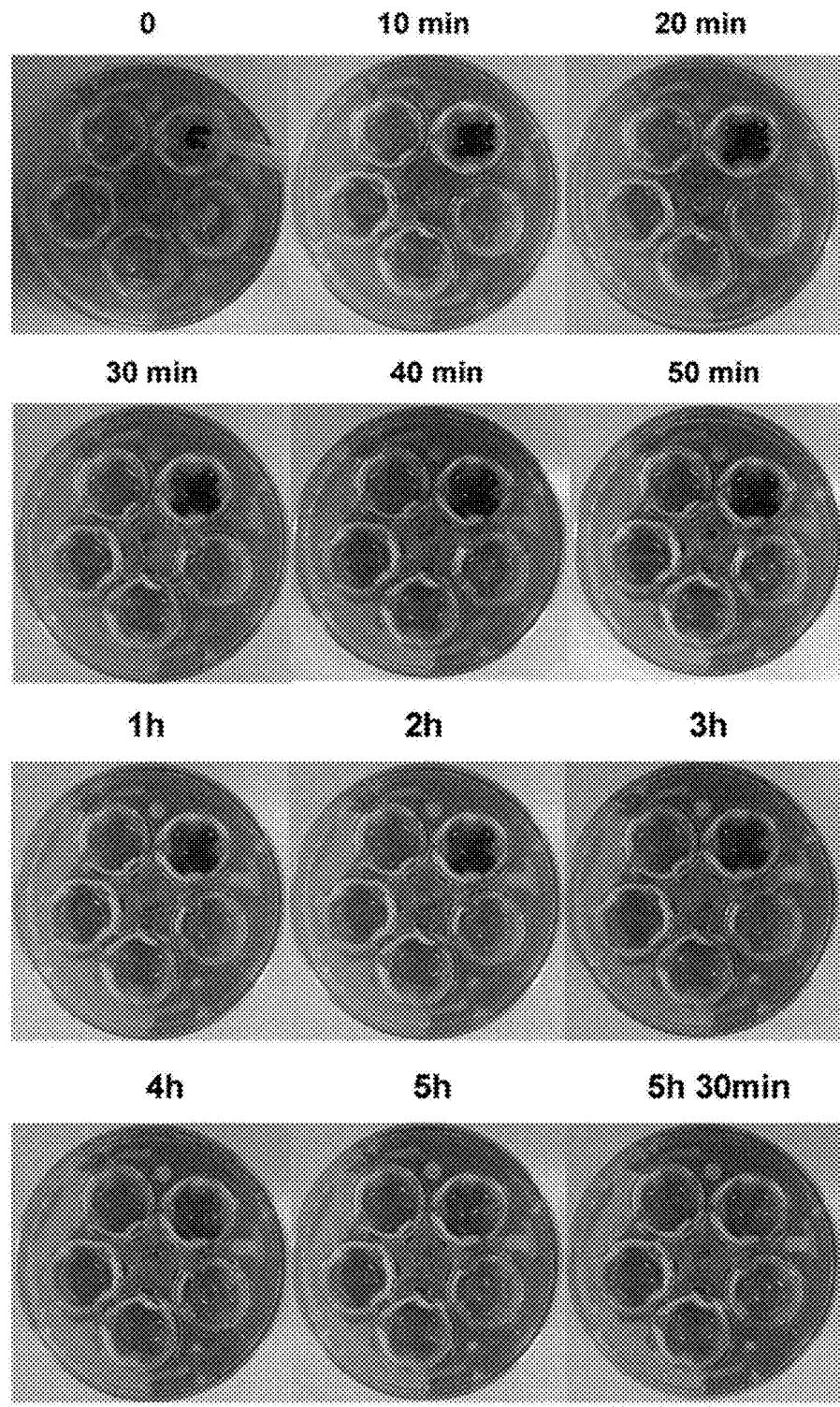

FIGS. 9 to 11 are views illustrating circulation of the media of samples 1 to 3 in which trans-wells are inserted, using a trepan-blue staining reagent under a dynamic culture condition.

The wall surface of the trans-wells is treated with a membrane to facilitate the exchange of the medium, and the bottom surface is configured to enable a cell culture.

In this case, 10 μl of trepan-blue staining reagent was dropped into one trans-well to observe circulation of the medium. The staining reagent was dropped and observed for 1 hour at the intervals of 10 minutes followed by for 5 hours and 30 minutes at the intervals of 1 hour.

Comparing FIGS. 9 to 11, the circulation of the medium in the interior of the trans-wells can be controlled by adjusting the capacity of the medium which is run in the cell culture vessel. The smaller the capacity of the medium, the more vigorous the circulation of the medium in the interior of the trans-well occurs.

Figure 12A:
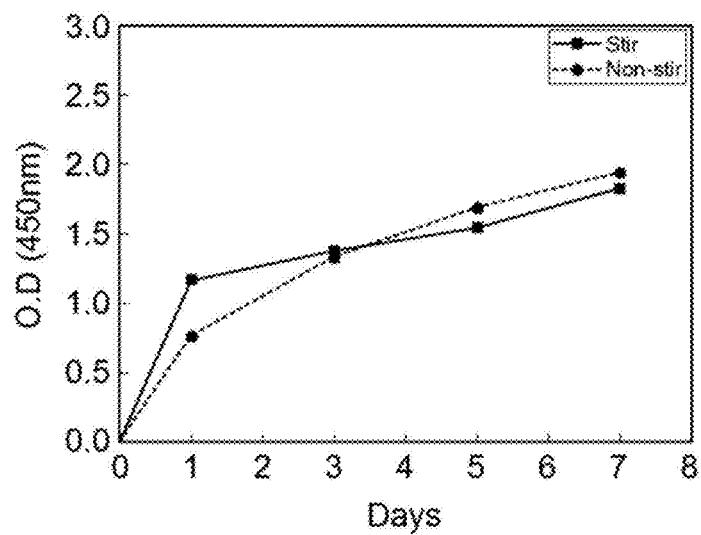
FIGS. 12a and 12b are views showing the viability confirmation by a cell proliferation and a live-dead assay of the tissues cultured three-dimensionally through a collagen sponge.
Figure 12B:
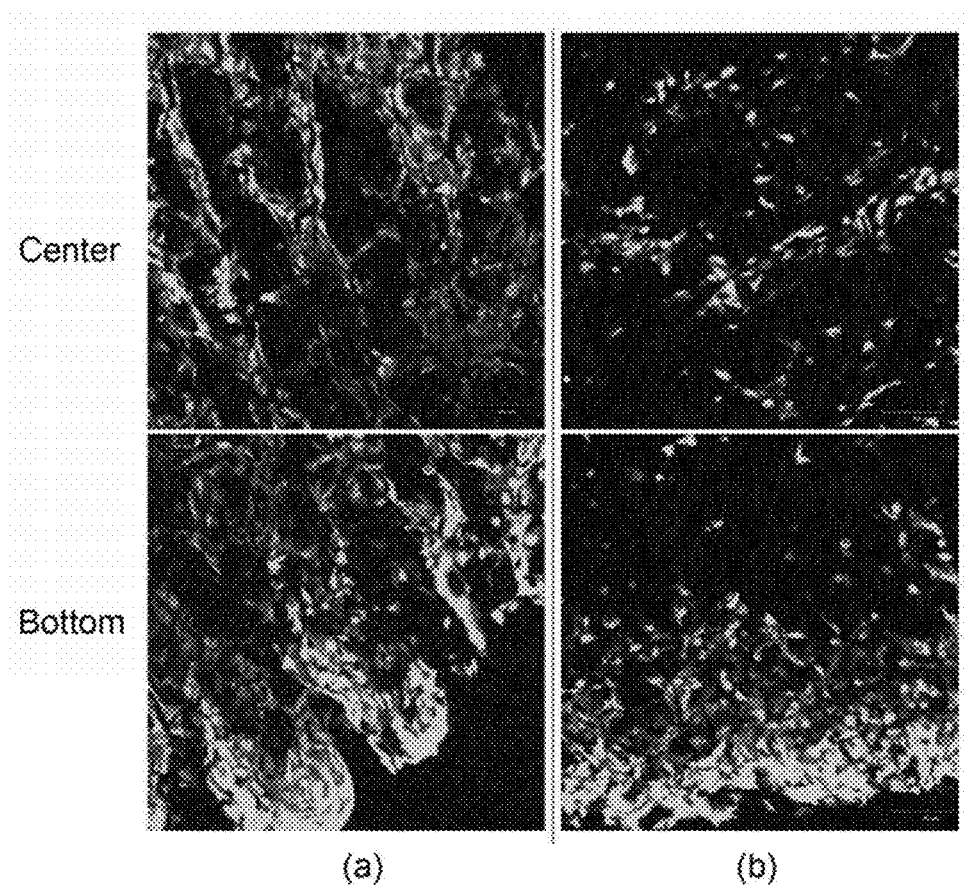

FIGS. 12a and 12b are views showing the viability confirmation by a cell proliferation and a live-dead assay of the tissues cultured three-dimensionally through a collagen sponge.

FIG. 12a is a graph related to confirmation of A cell proliferations (CCK-8 assay).

Step 1: The collagen sponge from Collacote Co., Ltd. was cut into a size of 2×5×5 mm (w×h×d), and HepG2 cells were injected into one collagen sponge at 5×10$^4$/10 μl.

Step 2: The cell-injected collagen sponge was transferred to a Petri culture vessel containing 9 ml of a medium after 3 hours elapsed, and cultured for a day so that the cells could be adhered to the collagen sponge sufficiently.

Step 3: In the next day, the collagen sponge was transferred to sample 3 of the cell culture vessel in which the trans-wells were inserted, and separated into a static culture environment and a dynamic culture environment (100 rpm) respectively to culture for a long period of time.

Step 4: The CCK-8 reagent, which confirms the cell viability of 50 μl, and the culture medium of 500 μl were premixed in the e-tube.

Step 5: The cultured collagen sponge was picked with forceps and transferred to a mixed medium to which the CCK-8 reagent is added to culture it for 2 hours.

Step 6: 100 μl of the medium was dispensed into a 96-well plate, and an absorbance was measured at 450 nm.

FIG. 12b is a view showing a B-cell viability confirmation (Live-dead assay).

The columns (a) and (b) of FIG. 12b show a dynamic culture condition and a static culture condition, respectively.

Step 1: Three-dimensional HepG2 cell tissues cultured for 1 week and 2 weeks under the static culture environment and the dynamic culture environment were photographed through a live-dead assay by a confocal fluorescence microscope.

Step 2: The live cells were expressed and observed as green fluorescence and the dead cells were expressed and observed as red fluorescence.

Step 3: Since there is a feeling of thickness of the collagen sponge, several pictures were photographed with Z-stack to combine them.

Comparing FIG. 12b (a), it can be confirmed that the number of cells survived at the initial stage (culture for a day) under the dynamic culture condition is more than those under the static culture condition.

Comparing FIGS. 12b (a) and 12b (b), it can be confirmed that the cells under the static culture condition are concentrated at the bottom surface of the collagen sponge rather than at the center of the collagen sponge, while the cells under the dynamic culture condition are evenly distributed in both the center and bottom surfaces. The above shows that the cells grown in the collagen sponge for 3D culture are more uniformly distributed and grown under the dynamic culture condition than under the static culture condition.

Figure 13A:
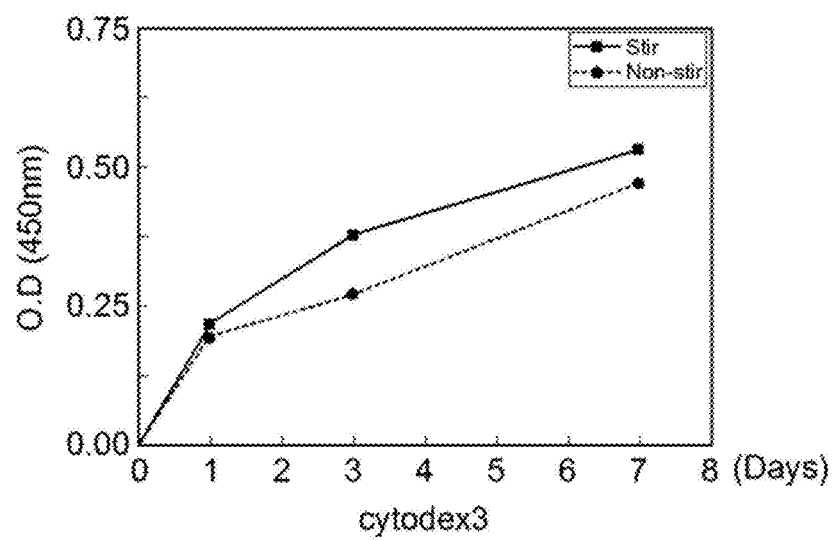
FIGS. 13a and 13b are views showing the viability confirmation by a two-dimensional mass culture of HepG2 cell proliferation and a live-dead assay through Cytodex 3.
Figure 13B:
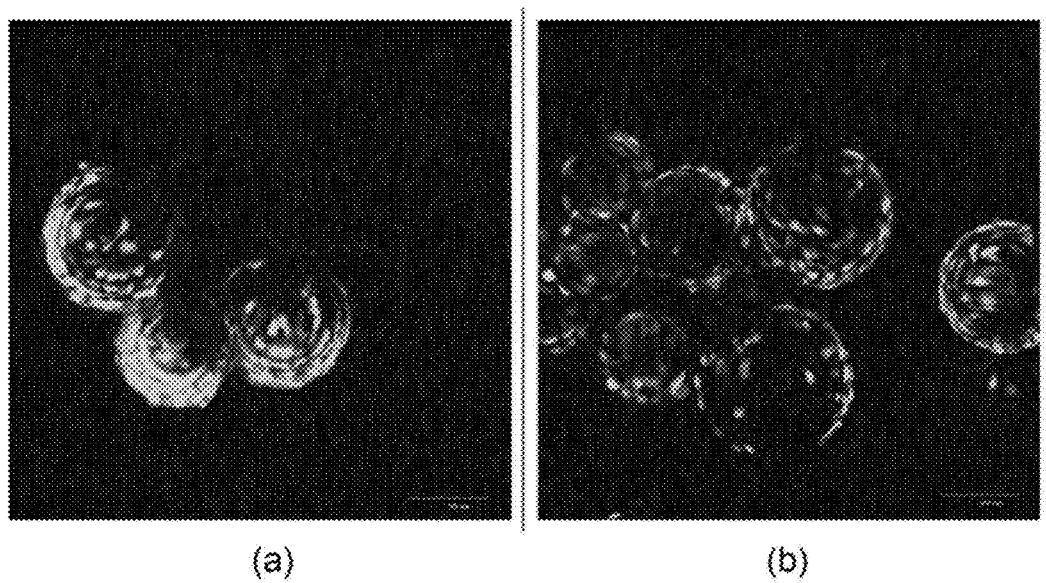

FIGS. 13a and 13b are views showing the viability confirmation by a two-dimensional mass culture of HepG2 cell proliferation and a live-dead assay through Cytodex 3.

FIG. 13a is a graph related to confirmation of A cell proliferations (CCK-8 assay).

Step 1: Trans-wells were inserted into sample 2, and 20 mg per a well of Cytodex 3 from GE Healthcare and 5×10$^4$ cells of HepG2 cells were mixed and injected.

Step 2: The cells were divided to the static culture condition and the dynamic culture condition and cultured for a long period of time. In the dynamic culture condition, the cells were stirred at 100 rpm with the stirring member for 30 minutes, and stopped and cultured for 2 minutes.

Step 3: The CCK-8 reagent, which confirms the cell viability of 100 μl, and the culture medium of 900 μl were premixed in the e-tube.

Step 4: 100 μl of HepG2 cells adhered to Cytodex 3 in trans-well was transferred to the e-tube containing the CCK-8 mixed medium, and then cultured for 2 hours.

Step 5: After the e-tube is stirred uniformly, the adhered HepG2-Cytodex 3 was submerged in the e-tube.

Step 6: 100 μl of the medium was dispensed into a 96-well plate, and absorbance was measured at 450 nm.

FIG. 13b is a view showing a B-cell viability confirmation (Live-dead assay).

The columns (a) and (b) of FIG. 13 show a dynamic culture condition and a static culture condition, respectively.

Step 1: Cytodex 3 cultured for 1 week under the static culture environment and the dynamic culture environment was photographed through a live-dead assay by a confocal fluorescence microscope.

Step 2: The live cells were expressed and observed as green fluorescence and the dead cells were expressed and observed as red fluorescence.

Step 3: After several pictures were photographed with Z-stack, they were combined together.

Comparing FIGS. 13(a) and 13(b), it can be seen that the number of the viable cells is much increased under the dynamic culture condition than the static culture conditions.

Figure 14:
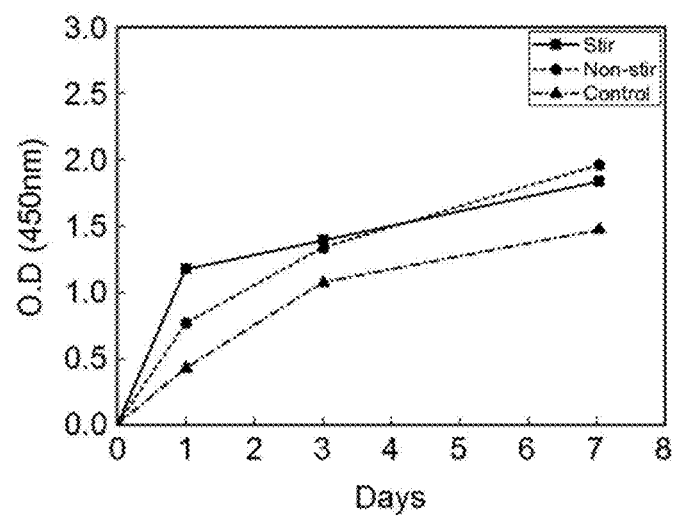
FIG. 14 is a graph related to HepG2 cell proliferation cultured through a collagen sponge.

FIG. 14 is a graph related to HepG2 cell proliferation cultured through a collagen sponge.

The graph of FIG. 14 shows the proliferation of HepG2 cells cultured under the same culture condition as the experiment described above with reference to FIG. 12.

Specifically, the graphs labeled by 'Stir' and 'Non-stir' show the cell growth rates over time in the dynamic culture condition and the static culture condition using the cell culture vessel according to one embodiment of the present invention, respectively.

Further, the graph indicated by 'Control' shows the cell growth rate over time under the condition that the stirring member (a stirrer bar or a magnetic bar) rotates using a culture vessel having no recess portion (a dent portion).

Referring to the graph of FIG. 14, it can be confirmed that the culture vessel according to an embodiment of the present invention, i.e., the culture vessel whose bottom surface is configured to locate a recess portion in which a stirring member is disposed, is higher in the cell growth rate than the conventional culture vessel.

What is claimed is:

1. A cell culture vessel comprising:
   a first vessel with a recess portion formed, wherein the recess portion is a space where a stirring member is disposed therein, and
   a second vessel configured to be inserted in the interior of the first vessel and having a hole for allowing a solvent accommodated in the first vessel to pass through the interior thereof,
   wherein the recess portion is the space formed integrally with the first vessel so as to protrude downward from a portion of a bottom surface of the first vessel, wherein the bottom surface of the first vessel has an annular adherent culture space is separated from the stirring member by the formation of the recess portion;
   wherein the recess portion includes a first surface and a second surface connected to the first surface;
   wherein the second surface, the bottom surface of the first vessel, and the longitudinal direction of the stirring member are each configured to be parallel;
   wherein the first surface surrounds the second surface, thereby forming a clearance space between the annular adherent culture space and a base surface supporting the cell culture vessel which is in contact with the second surface; and
   wherein the center of the recess portion substantially coincides with the centers of the first vessel and the second vessel.

2. The cell culture vessel according to claim 1, wherein the area of the recess portion is set to sufficiently accommodate the stirring member in the recess portion and to cause a cell adhesion to occur on the bottom surface of the first vessel.

3. The cell culture vessel according to claim 2, wherein the area of the second surface of the recess portion is 70% or less of the area of the bottom surface of the first vessel.

4. The cell culture vessel according to claim 1, wherein a third vessel is disposed in the interior of the second vessel and has a hole for allowing a solvent accommodated in the second vessel to pass through the interior thereof.

5. The cell culture vessel according to claim 1, wherein the stirring member is a magnetic stirrer.

6. The cell culture vessel according to claim 1, wherein an upper end of the second vessel has a latching portion that is latched on to the first vessel.

7. A cell culture vessel comprising a plurality of the culture vessels according to claim 1, wherein the first vessels of the plurality of culture vessels are integrally formed into a plate.

* * * * *